Figure 1:
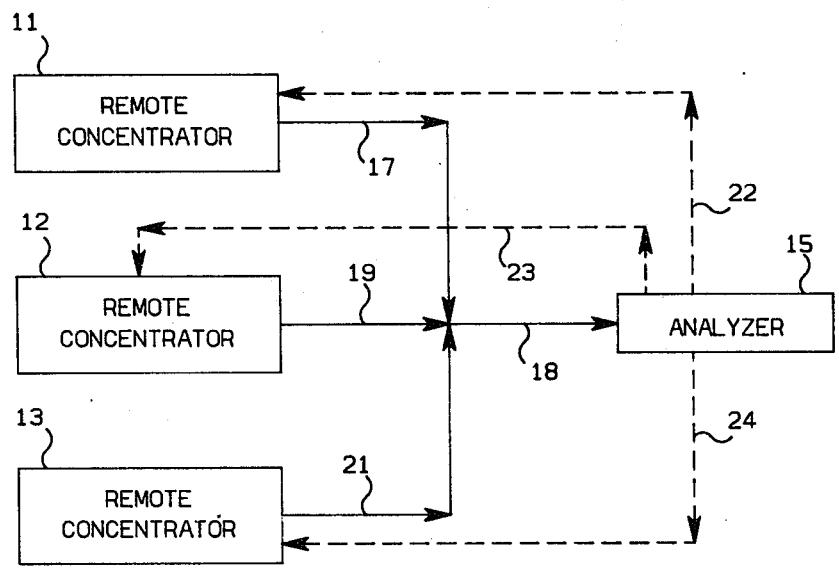

United States Patent [19]

Dennis

[11] 4,399,688
[45] Aug. 23, 1983

[54] AIR POLLUTION DETECTION

[75] Inventor: William H. Dennis, Bartlesville, Okla.

[73] Assignee: Phillips Phillips Petroleum, Bartlesville, Okla.

[21] Appl. No.: 264,512

[22] Filed: May 18, 1981

[51] Int. Cl.³ .................. G01N 1/22; G01N 31/06
[52] U.S. Cl. ................... 73/23.1; 73/364.81; 73/364.83
[58] Field of Search ............... 73/23.1, 863.21, 864.81, 73/864.83

[56] References Cited
U.S. PATENT DOCUMENTS

| | | | |
|---|---|---|---|
| 3,675,466 | 7/1972 | Linenberg | 73/23.1 X |
| 3,733,908 | 5/1973 | Linenberg | 73/864.81 |
| 3,797,318 | 3/1974 | Palm | 73/864.81 |
| 3,807,217 | 4/1974 | Wilkins et al. | 73/23.1 |
| 3,897,679 | 8/1975 | Guild | 73/23.1 X |
| 4,084,440 | 4/1978 | Carpenter et al. | 73/864.81 |
| 4,128,008 | 12/1978 | Linenberg | 73/864.81 |
| 4,208,912 | 6/1980 | Baldeck | 73/863.21 |
| 4,215,563 | 8/1980 | Clardy et al. | 73/23.1 |

Primary Examiner—James J. Gill

[57] ABSTRACT

At least one air pollutant is concentrated at the source from which the sample of air is obtained. The thus concentrated at least one air pollutant is provided through conduits to a central analyzer for analysis. Concentration of the air pollutant results in reducing transport losses and also the sensitivity of the detector utilized to detect the at least one air pollutant can be greatly increased.

12 Claims, 2 Drawing Figures

AIR POLLUTION DETECTION

This invention relates to detection of air pollution. In one aspect this invention relates to method and apparatus for transporting air pollutants from the sample source to a central analyzer.

The air quality at industrial sites such as chemical manufacturing facilities is an important consideration with respect to the safety of employees working at such sites. The presence in the air of pollutants such as sulfur dioxide, nitrogen oxide, carbon monoxide or hydrogen sulfide in concentrations even as small as one part per billion may not be tolerable and may be life endangering.

It is common to analyze the air at various points around an industrial site or other site where air pollution may be a problem to continuously monitor the air quality. This is typically accomplished by moving air from different locations through conduits to a central analyzer which is utilized to provide information concerning the concentration of various pollutants in the air. However, it may be difficult to obtain a true analysis of the concentration of a pollutant at a certain location because it may be difficult to transport various pollutants through metal or plastic tubing for the long distances required because the pollutants may react with the sample lines or other components in the air during the time such pollutants are being transported to the central analyzer location. It is thus an object of this invention to provide method and apparatus for transporting air pollutants from the sample source to a central analyzer in such a manner that a true indication of the concentration of a particular air pollutant at some location remote from the central analyzer is provided.

In accordance with the present invention, method and apparatus is provided for concentrating an air pollutant at the source from which the sample of air is obtained. The thus concentrated air pollutant is provided through sample conduits to a central analyzer for analysis. Concentration of the air pollutant results in reduced transport losses and also the sensitivity of the detector can be greatly increased.

In general, concentration of air pollutants at the sample source may be accomplished by providing the air sample to a column containing an adsorbing material. The air sample is allowed to flow through the adsorbing material for a desired length of time and then the flow of the air sample is terminated. A carrier fluid is then allowed to flow through the adsorbing material while the adsorbing material is quickly heated so as to cause desorption. This results in the air pollutants being concentrated in a very small volume of the carrier fluid. The thus concentrated air pollutants are then provided by means of the carrier fluid to the central analyzer for analysis.

Figure 2:
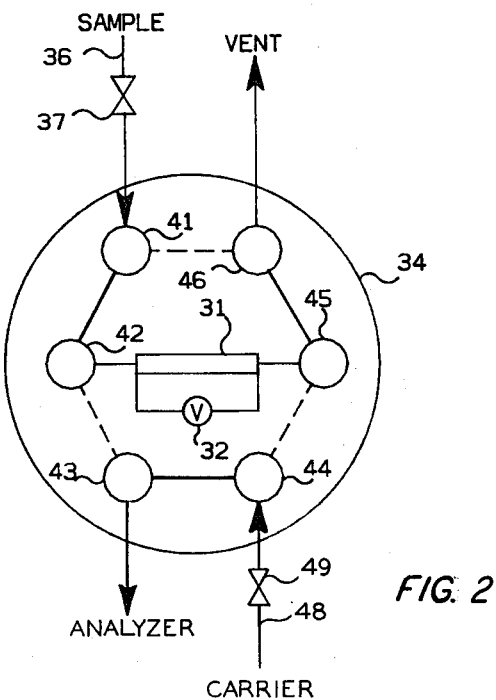

Other objects and advantages of the invention will be apparent from the foregoing brief description of the invention and the claims as well as the detailed description of the drawings in which:

FIG. 1 is a diagrammatic illustration of a plurality of remote concentrators used to provide samples to a central analyzer; and FIG. 2 is a diagrammatic illustration of one of the remote concentrators of FIG. 1.

Referring now to FIG. 1, there is illustrated three remote concentrators 11, 12 and 13. The number of remote concentrators used will depend on the number of locations from which air samples must be obtained. Each remote concentrator is located in the area where the air sample is being taken.

Remote concentrators 11-13 are used to concentrate air pollutants for transport to the analyzer 15. The manner in which this is accomplished will be described more fully hereinafter. The concentrated sample of air pollutants is provided from the remote concentrator 11 through the combination of conduit means 17 and 18 to the analyzer 15. In like manner, a concentrated sample of air pollutants is provided from the remote concentrator 12 through the combination of conduit means 19 and 18 to the analyzer 15 and a concentrated sample of air pollutants is provided from the remote concentrator 13 through the combination of conduit means 21 and 18.

The analyzer 15 may be a dedicated sensor such as a hydrogen sulfide sensitive tape or a form of ultraviolet or infrared detector sensitized to a particular pollutant. Preferably, the analyzer 15 is a more sophisticated system such as a gas chromatograph or a mass spectrometer programmed to separate and quantify one or more pollutants in the concentrated sample. The analyzer 15 is also preferably a programmable device which can be programmed to control each of the remote concentrators 11-13 as will be more fully described hereinafter. A preferred analyzer 15 is the Optichrom 2100 Process Chromatograph System manufactured by Applied Automation, Inc. Bartlesville, Ok.

Control signal 22 is provided from the analyzer 15 to the remote concentrator 11 to provide a means for controlling the remote concentrator 11 so as to provide the concentrated sample to the analyzer 15 at a desired time and further to control the manner in which the sample is concentrated. In like manner, control signal 23 is utilized to control the remote concentrator 12 and control signal 24 is utilized to control the remote concentrator 13. The manner in which the remote concentrators 11-13 are controlled will be described more fully hereinafter.

The conduits utilized to transport air pollutants from the sample site to a central analyzer may be several hundred feet in length. Use of the remote concentrators 11-13 provides a means by which concentrated air pollutant samples may be provided from the remote locations to a central analyzer in such a manner that representative indications of the concentration of particular air pollutants at a particular remote location at a site may be obtained. If the sample site is not more than about 10 ft from the central analyzer, the remote concentration will generally not provide any benefit.

Referring now to FIG. 2, there is illustrated one remote concentrator system. The principal element of the remote concentrator system is the adsorbing column 31 which contains an adsorbing material. The adsorbing column 31 may have any suitable configuration such as a straight tube or a coiled tube. Preferably, the adsorbing column 31, is formed from stainless steel tubing and inside diameter of 1/16 inch with 0.05 inch wall thickness. The thin walls and low mass of the tubing allows the tubing to rapidly return to near ambient temperatures after heating as required for desorption.

The adsorbing column 31 may be filled with any suitable adsorbing material. The composition of the adsorbing material will be determined by the particular pollutants which are of interest. A number of different adsorbing materials are commercially available and are well known to those skilled in the art of analyzing for air pollution.

Preferably, means is provided for heating the adsorbing column 31 so as to desorb pollutants contained in the adsorbing material. Preferably, a voltage source 32 is utilized to drive a current through the adsorbing column 31 so as to heat the adsorbing column 31. For the preferred adsorbing column described, the electrical resistance end to end is about $0.5\Omega$ so that a five volt source could drive 10 amps through the adsorbing column 31. Typically, a five second pulse of current heats the tubing to about 500° F. Factors such as the melting point of the adsorbing material and the bonding forces between the adsorbing material and the pollutants determine the amount of heat which must be applied to the adsorbing column 31. Again, the amount of heat which must be supplied to the adsorbing material so as to cause desorption is generally specified by the commercial suppliers of such materials.

Heat desorption could also be accomplished by techniques such as heating tape, hot air, microwaves or other similar heating techniques. Preferably, the heating technique utilized must be such as to cause a fast rise time in the temperature of the adsorbing column 31 so as to provide near instantaneous desorption of the pollutants contained in the adsorbing column 31.

It is noted that any other suitable desorption technique may be utilized although heat desorption is preferred because it can be accomplished quickly and thus provides better concentration. Desorption techniques such as use of a carrier for which the pollutant has a preference over the absorbing material or with which the pollutant will react chemically may be used.

Any suitable valving system may be utilized in the remote concentration system so long as alternate flows of air being sampled and a carrier fluid may be provided to the adsorbing column 31. Preferably, a diaphragm switching valve such as the Model VIII sample valve manufactured by Applied Automation, Inc. is preferably used. The adsorbing column 31 is connected in place of the typical sample loop which would be associated with such a valve.

The sample valve 34 is essentially a two position valve. The solid lines between the ports of the sample valve 34 indicates the flow in the first position. The dotted lines between the ports of the sample valve 34 indicates the flow in the second position.

Air to be sampled is supplied through the combination of conduit means 36 and regulator 37 to the port 41 of the sample valve 34. With the sample valve 34 in the first position, the air flowing through conduit means 36 flows from port 41 to port 42 of the sample valve 34 and thus through the adsorbing column 31 to the port 45 of the sample valve 34. From the port 45, the air being sampled flows to port 46 and then is vented. The flow of air to be sampled to the adsorbing column 31 may be caused by an upstream pump or a downstream vacuum source or other suitable means for moving a fluid such as air.

A carrier fluid such as helium, purified air, nitrogen or other suitable fluid is provided through the combination of conduit means 48 and regulator 49 to the port 44 of the sample valve 34. With the sample valve 34 in the first position, the carrier flows from the port 44 to the port 43 and thus to the analyzer 15 illustrated in FIG. 1.

If the sample valve 34 is switched to the second position, the flow of air to the adsorbing column 31 will be terminated and air will flow from port 41 to port 46 and thus be vented. The flow of carrier will be diverted through the adsorbing column 31 as is illustrated by the dotted lines. Thus, a technique is provided for alternately passing air to be sampled and a carrier fluid through the adsorbing column 31.

In operation, a fixed volume of air to be sampled is passed through the adsorbing column 31. As an example, the regulator 37 may be set so as to provide 100 cc/minute of air to the adsorbing column 31. After a fixed length of time such as 10 minutes, the flow of air to the adsorbing column is automatically terminated by switching the sample valve 34 to a second position. Thus 1,000 cc of air will have been sampled.

Most of the normal constituents of air such as nitrogen and oxygen are not retained by the adsorbing material. Other constituents such as carbon dioxide and water vapor may or may not be collected, depending on the adsorbing material utilized. The pollutants of interest will be adsorbed by the adsorbing material and retained in the adsorbing column 31.

After the sample valve 34 is switched to the second position, the carrier fluid may be allowed to flow through the adsorbing column 31 for a short period of time while the adsorbing column 31 is maintained at ambient temperature so as to allow the purging of air and water vapor from the tube. The heating system for the adsorbing column is then activated and the temperature of the adsorbing column 31 is then increased so as to cause desorption. Preferably, the desorption takes place in about 5 seconds. Assuming that the flow regulator 49 is set so as to provide 1 cc per second of carrier fluid to the adsorbing column 31, the pollutants will have been concentrated in a 5 cc envelope of carrier fluid. This results in a concentration factor of 200. Obviously, other concentration factors could be obtained simply by changing the length of time that sample air flows through the adsorbing column 31, the rate at which the sample air flows through the adsorbing column 31, the rate at which the carrier fluid flows through the adsorbing column 31, or the time taken to desorb the pollutants contained in the adsorbing column 31.

The carrier fluid may be introduced into the adsorbing column 31 in the same direction or opposite direction as the flow of air. Preferably, the carrier fluid is passed through the adsorbing column 31 in the opposite direction that air is passed through the adsorbing column 31. The lighter concentration of air pollutants will be at the end of the adsorbing column 31 opposite the end at which the air is introduced. Introduction of the carrier fluid at the end of the adsorbing column 31 having the lighter concentration of air pollutants results in a greater concentration of the air pollutants in the carrier fluid.

Concentration of the pollutants, in the manner described, at the source from which the air sample is taken reduces transport losses for the pollutant samples as has been previously described. In addition, the greatly increased concentration of the pollutants allows the sensitivity of the analysis to be greatly increased and also improves the reliability of such analysis.

Automatic control may be utilized as previously described to provide concentrated pollutant samples sequentially from a large number of remote concentrators to a central analyzer. In this manner, accurate polluant analysis may be obtained from a number of areas at an industrial site or other locations where analysis is desirable using only a single analyzer.

The invention has been described in terms of a preferred embodiment as illustrated in FIGS. 1 and 2. Although the invention has been illustrated in terms of a preferred embodiment, reasonable modifications and variations are possible by those skilled in the art within the scope of the described invention and the appended claims.

That which is claimed is:

1. Apparatus for determining if at least one air pollutant is contained in air sampled at a first location, said apparatus comprising:

an adsorbing column located at said first location, wherein said adsorbing column contains an adsorbing material capable of adsorbing said at least one air pollutant;

means for passing air obtained from said first location through said adsorbing column for a first period of time;

means for passing a carrier fluid through said adsorbing column for a second period of time;

means for controlling the flow of said air and said carrier fluid to said adsorbing column in such a manner that said air and said carrier fluid are provided alternately to said adsorbing column;

means for desorbing said at least one pollutant, wherein said at least one pollutant is desorbed in a third period of time when said carrier fluid is flowing through said adsorbing column and wherein said third period of time is much less than said first period of time;

means for detecting the presence of said at least one air pollutant in a sample, wherein said means for detecting is located at a second location which is at least ten feet from said first location; and conduit means for providing said carrier fluid to said means for detecting, wherein a concentrated sample of said at least one pollutant is introduced into said carrier fluid when said carrier fluid is passing through said adsorbing column and said at least one pollutant is desorbed so as to provide a concentrated sample of said at least one pollutant through said conduit means to said means for detecting.

2. Apparatus in accordance with claim 1 wherein said carrier fluid is passed through said adsorbing column in the opposite direction that said air is passed through said adsorbing column.

3. Apparatus in accordance with claim 1 wherein said means for passing said air through said adsorbing column and said means for passing said carrier fluid through said adsorbing column comprises:

a sample valve means having at least first, second, third, fourth, fifth and sixth ports, said first and second ports being in fluid communication with each other, said third and fourth ports being in fluid communication with each other and said fifth and sixth ports being in fluid communication with each other when said sample valve is in a first position and said first and sixth ports being in fluid communication with each other, said second and third ports being in fluid communication with each other and said fourth and fifth ports being in fluid communication with each other when said sample valve is in a second position, said second and fifth ports being connected to each other in fluid communication through said adsorbing column;

means for providing air sampled at said first location to said first port;

means for venting said air from said sixth port;

means for providing said carrier fluid to said fourth port; and means for providing carrier fluid from said third port to said means for detecting.

4. Apparatus in accordance with claim 3 wherein said means for controlling the flow of said air and said carrier fluid to said adsorbing column comprises means for switching the position of said sample valve, wherein said air is supplied to said adsorbing column when said sample valve is in said first position and said carrier fluid is provided to said adsorbing column when said said sample valve is in said second position.

5. Apparatus in accordance with claim 1 wherein said means for desorbing said least one pollutant comprises means for heating said adsorbing column.

6. Apparatus in accordance with claim 5 wherein said adsorbing column is a stainless steel tube having a wall thickness of about 0.05 inches and said means for heating said adsorbing column comprises means for passing an electrical current through the walls of said stainless steel tube.

7. Apparatus in accordance with claim 1 wherein said means for detecting comprises a chomatographic analyzer.

8. Apparatus in accordance with claim 1 wherein said second location is at least one hundred feet from said first location.

9. A method for determining if at least one air pollutant is contained in air sampled at a first location, said method comprising the steps of:

passing air obtained from first location in contact with an adsorbing material for a first period of time, wherein said adsorbing material is capable of adsorbing said at least one pollutant;

passing a carrier fluid in contact with said adsorbing material after the end of said first period of time;

desorbing said at least one pollutant from said adsorbing material in a second period of time when said carrier fluid is being contacted with said adsorbing material to thereby desorb said at least one pollutant into said carrier fluid, wherein said second period of time is much less than first period of time; and passing said carrier fluid containing said at least one pollutant through a conduit to a detector capable of detecting the presence of said at least one pollutant in a sample, wherein said detector is located at a second location which is at least ten feet from said first location.

10. A method in accordance with claim 9 wherein said carrier fluid is passed in contact with said adsorbing material in the opposite direction that said air is passed in contact with said adsorbing material.

11. A method in accordance with claim 9 wherein said step of desorbing said at least one pollutant comprises heating said adsorbing material for said second period of time.

12. A method in accordance with claim 9 wherein said second location is at least one hundred feet from said first location.

* * * * *